United States Patent

Takekoshi et al.

[11] Patent Number: 5,591,800
[45] Date of Patent: Jan. 7, 1997

[54] METHOD FOR POLYMERIZING MACROCYCLIC POLY(ALKYLENE DICARBOXYLATE) OLIGOMERS

[75] Inventors: Tohru Takekoshi, Scotia; Eric J. Pearce, Ballston Lake, both of N.Y.

[73] Assignee: General Electric Company, Schenectady, N.Y.

[21] Appl. No.: 565,366

[22] Filed: Nov. 30, 1995

Related U.S. Application Data

[62] Division of Ser. No. 371,715, Jan. 12, 1995, Pat. No. 5,527,976.

[51] Int. Cl.⁶ .............................. C08K 3/10; C08G 63/85
[52] U.S. Cl. .............................. 524/783; 528/279; 502/50
[58] Field of Search .............................. 528/279; 524/783; 502/150

[56] References Cited

U.S. PATENT DOCUMENTS

| | | | |
|---|---|---|---|
| 5,039,783 | 8/1991 | Brunelle et al. | 528/272 |
| 5,214,158 | 5/1993 | Brunelle et al. | 549/267 |
| 5,231,161 | 7/1993 | Brunelle et al. | 528/272 |
| 5,321,117 | 6/1994 | Brunelle | 528/272 |
| 5,386,037 | 1/1995 | Takekoshi et al. | 549/206 |
| 5,387,666 | 2/1995 | Takekoshi et al. | 528/283 |
| 5,389,719 | 2/1995 | Takekoshi et al. | 524/784 |
| 5,466,744 | 11/1995 | Evans et al. | 524/714 |

*Primary Examiner*—Samuel A. Acquah
*Attorney, Agent, or Firm*—William H. Pittman

[57] ABSTRACT

Macrocyclic polyester oligomers are converted to linear polyesters by contact at a temperature of about 160°–300° C. with a cyclic titanium catalyst such as di-(1-butyl)-2,2-dimethylpropane-1,3-dioxytitanate, bis(2,2-dimethyl-1,3-propylene) titanate or 1-(1-butoxy)-4-methyl-2,6,7-trioxa-1-titanabicyclo[2.2.2]octane. Such catalysts have high activity and produce linear or branched polyesters of very high molecular weight.

12 Claims, No Drawings

METHOD FOR POLYMERIZING MACROCYCLIC POLY(ALKYLENE DICARBOXYLATE) OLIGOMERS

This application is a division of application Ser. No. 08/371,715, filed Jan. 12, 1995, now U.S. Pat. No. 5,527,976.

BACKGROUND OF THE INVENTION

This invention relates to the polymerization of macrocyclic polyester oligomer compositions. More particularly, it relates to an improved method for such polymerization which is capable of producing novel branched polyesters.

The preparation of macrocyclic poly(alkylene dicarboxylate) oligomers and their polymerization to linear polyesters is described in U.S. Pat. Nos. 5,039,783, 5,214,158 and 5,231,161 and in copending, commonly owned applications Ser. No. 08/369,986 now U.S. Pat. No. 5,466,744 and Ser. No. 07/978,583 now U.S. Pat. No. 5,321,117. The catalysts employed for such polymerization include various organotin compounds and titanate esters.

Polymerization using these catalysts is quite successful and affords polyesters having excellent properties and a wide variety of potential applications. However, the catalysts are somewhat sensitive to impurities present in the macrocyclic polyesters, particularly acidic impurities which can include water, hydroxy compounds and carboxylic acids and their anhydrides.

In the presence of such impurities, the catalyst may be partially deactivated and polymerization may be incomplete or may yield polymers with low weight average molecular weights. Attempts to increase polymer yield by increasing the proportion of catalyst in the polymerization mixture cause significant further reductions in the molecular weight of the linear polymer, since the catalyst becomes part of the polymer end group and increased amounts of catalyst compete for the same proportions of structural units in the macrocyclic oligomers.

In copending, commonly owned applications Ser. Nos. 08/262,793, 08/262,795 and 08/262,799 now U.S. Pat. Nos. 5,386,037; 5,389,719, and 5,387,666 respectively, there are disclosed several cyclic tin catalysts which offer improvements with respect to the above-described problems. However, these tin compounds are expensive to prepare and there are environmental and health concerns about their use, It would be desirable, therefore, to develop safe and inexpensive catalysts with high activity for the polymerization of macrocyclic oligomers containing increased proportions of impurities, especially acidic impurities. It would be further desirable to provide a means for inexpensively converting macrocyclic oligomer compositions to branched polyesters having improved dimensional stability, for use as load-bearing members in automobiles and the like.

SUMMARY OF INVENTION

The present invention provides a method for producing polyesters of high molecular weight and high dimensional stability from macrocyclic oligomers. Said oligomers and polyesters may be employed in the fabrication of fiber-reinforced composites and the like. The polyester products include branched polyesters, whose proportion in the product may be varied and which contribute to dimensional stability.

The invention in one of its aspects is a method for preparing a polyester which comprises contacting, at a temperature within the range of about 160°–300° C., at least one macrocyclic polyester oligomer comprising structural units of the formula

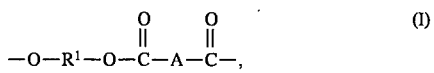

wherein $R^1$ is an alkylene or mono-or polyoxyalkylene radical containing a straight chain of about 2–8 atoms and A is a m- or p-linked monocyclic aromatic or alicyclic radical, with at least one titanium-containing macrocyclic polyester oligomer polymerization catalyst having, at least in part, the formula

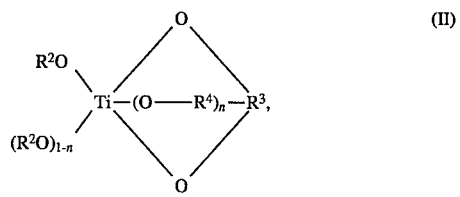

wherein:

$R^2$ is an alkyl radical, or the two $R^2$ radicals taken together form a divalent saturated aliphatic hydrocarbon radical;

$R^3$ is a $C_{2-10}$ divalent or trivalent saturated aliphatic hydrocarbon radical;

$R^4$ is a methylene or ethylene radical; and n is 0 or 1.

Another aspect of the invention is a polyester prepared by the above-described method. Polyesters of this type have unique structural characteristics, as explained in detail hereinafter.

Still another aspect of the invention is a titanabicyclo compound of the formula

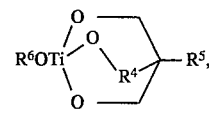

wherein $R^4$ is as previously defined, $R^5$ is hydrogen or $C_{1-7}$ alkyl and $R^6$ is alkyl as defined for $R^2$.

DETAILED DESCRIPTION; PREFERRED EMBODIMENTS

The macrocyclic polyester oligomers which are polymerized according to this invention may be prepared by contacting at least one diol of the formula HO—$R^1$—OH and at least one diacid chloride of the formula

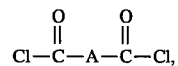

under substantially anhydrous conditions and in the presence of a substantially water-immiscible organic solvent, with at least one unhindered tertiary amine; said contact being conducted at a temperature from about −25° to about +25° C. This procedure is described in detail in the aforementioned patents, and it is therefore deemed unnecessary to provide a detailed explanation herein. In most instances, the products are mixtures of macrocyclic oligomers having differing degrees of polymerization. The preferred oligomers in many instances are poly(butylene terephthalate), poly(ethylene terephthalate) and copolymers thereof.

According to the present invention, the macrocyclic polyester oligomers are converted to linear or branched polyesters, often of high molecular weight, by contact with a titanium-containing macrocyclic polyester oligomer polymerization catalyst. The catalysts employed are those having, at least in part, formula II. In that formula, the $R^2$ values may be alkyl radicals, typically $C_{1-10}$ alkyl and especially primary and secondary alkyl radicals. Also included are spiro compounds wherein the $R^2$ radicals together form a divalent saturated aliphatic hydrocarbon radical, typically identical to $R^3$ as defined hereinafter.

The $R^3$ value may be a divalent (when n is 0) or trivalent (when n is 1) saturated linear or branched, preferably branched, aliphatic hydrocarbon radical containing 2–10 and preferably 3–10 carbon atoms. It usually has a chain of 2–3 and preferably 3 carbon atoms separating the oxygen atoms. $R^4$, when present, is a methylene or ethylene radical; it should be noted that when $R^4$ is present the second $R^2O$ moiety attached to titanium is absent.

The following are typical of titanium compounds employed as catalysts according to the present invention:

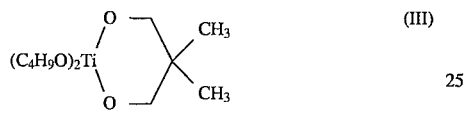
(III)

Di-(1-butyl)2,2-dimethylpropane-1,3-dioxytitanate

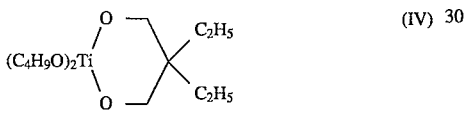
(IV)

Di-(1-butyl)2,2-diethylpropane-1,3-dioxytitanate

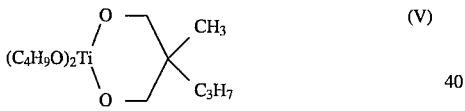
(V)

Di-(1-butyl)2-(1-propyl)-2-methylpropane-
1,3-dioxytitanate

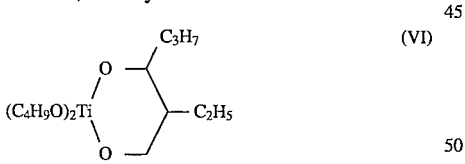
(VI)

Di-(1-butyl)2-ethylhexane-1,3-dioxytitanate

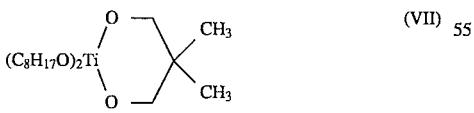
(VII)

Di-(2-ethyl-1-hexyl)2,2-dimethylpropane-
1,3-dioxytitanate

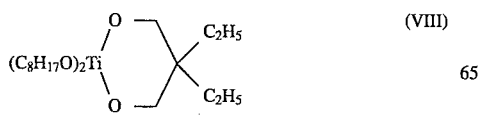
(VIII)

Di-(2-ethyl-1-hexyl)2,2-diethylpropane-
1,3-dioxytitanate

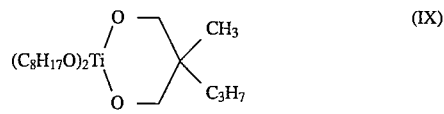
(IX)

Di-(2-ethyl-1-hexyl)2-(1-propyl)-2-methylpropane-
1,3-dioxytitanate

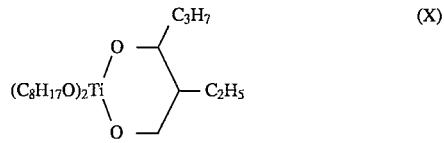
(X)

Di-(2-ethylhexyl)2-ethylhexane-1,3-dioxytitanate

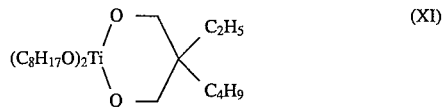
(XI)

Di-(2-ethylhexyl)2-ethylhexane-1,3-dioxytitanate

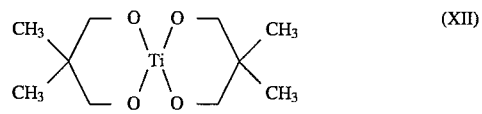
(XII)

Bis(2,2-dimethyl-1,3-propylene)titanate

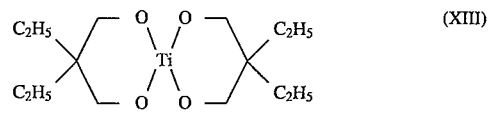
(XIII)

Bis(2,2-diethyl-1,3-propylene)titanate

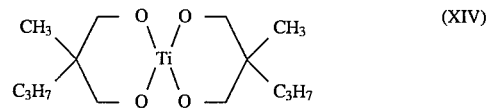
(XIV)

Bis[2-(1-propyl)-2-methyl-1,3-propylene]titanate

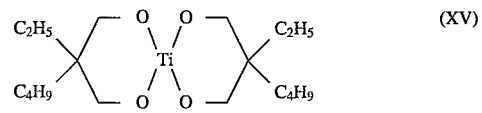
(XV)

Bis[2-(1-propyl)-2-ethyl-1,3-propylene]titanate

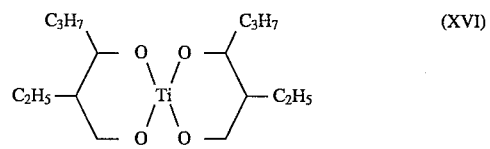
(XVI)

Bis(2-ethyl-1,3-hexylene)titanate

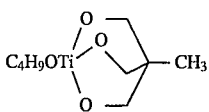 (XVII)

1-(1-Butoxy)-4-methyl-2,6,7-trioxa-1-titanabicyclo[2.2.2]octane

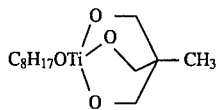 (XVIII)

1-(2-ethyl-1-hexoxy)-4-methyl-2,6,7-trioxa-1-titanabicyclo[2.2.2]octane

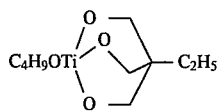 (XIX)

1-(1-Butoxy)-4-ethyl-2,6,7-trioxa-1-titanabicyclo[2.2.2]octane

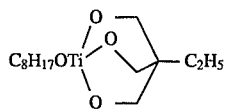 (XX)

1-(2-ethyl-1-hexoxy)-4-ethyl-2,6,7-trioxa-1-titanabicyclo[2.2.2]octane

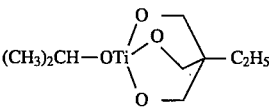 (XXI)

1-(2-Propoxy)-4-ethyl-2,6,7-trioxa-1-titanabicyclo[2.2.2]octane.

The titanium-containing catalysts of formula II wherein n is 0 and $R^2$ is alkyl are illustrated by formulas III–XI. They may be prepared by the reaction of substantially equimolar proportions of a tetraalkyl titanate and an alkanediol such as 2,2-dimethyl-1,3-propanediol, 2,2-diethyl-1,3-propanediol, 2-methyl-2-(1-propyl)-1,3-propanediol or 2-ethyl-1,3-hexanediol. By "substantially equimolar" is meant within about 5 mole percent of equimolar, any excess generally being of the diol. The reaction is normally conducted at reduced pressure in an inert atmosphere, typically nitrogen, with the removal by distillation of alkanol which is formed as a by-product. The product is typically a liquid or paste.

The compounds of formula II in which the two $R^2$ radicals taken together are alkylene are spiro compounds, illustrated by formulas XII–XVI. They may be prepared similarly, except that the molar ratio of diol to tetraalkyl titanate is 2:1 or slightly (e.g., up to about 5 mole percent)in excess. They are typically crystalline solids having melting points above 200° C. and often above 300° C.

Bicyclo compounds wherein n is 1 are illustrated by formulas XVII–XXI. They may be obtained by the similarly conducted reaction of substantially equimolar proportions of a tetraalkyl titanate and a triol of the formula

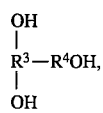

wherein $R^3$ and $R^4$ are as previously defined, such as 2,2-bis(hydroxymethyl)-1-butanol or 2,2-bis(hydroxymethyl)-1-pentanol. They are also typically crystalline solids melting above 300° C.

As described hereinafter, it is frequently advantageous to employ liquids rather than solids as catalysts. By the reaction of 2–3 moles of tetraalkyl titanate with 1 mole of triol, a mixed catalyst containing tetraalkyl titanate species and bicyclo species of formula II in which n is 1, of the type represented by formulas XVII–XXI, which is in liquid form at ambient temperatures, may be obtained. This is unexpected, since simple mixtures of the tetraalkyl titanate and the previously prepared triol titanate are heterogeneous. Similar mixed catalysts in liquid form may be obtained by the reaction of tetraalkyl titanate with a mixture of diol and triol, the molar ratios of tetraalkyl titanate to diol and triol being about 1.2–2.0:1 and about 3–4:1, respectively.

The preparation of titanate compounds useful as catalysts is illustrated by the following examples.

EXAMPLE 1

A mixture of 7.810 grams (13.83 mmol.) of tetra-2-ethyl-1-hexyl titanate and 1.828 grams (13.83 mmol.) of 2,2-diethyl-1,3-propanediol was charged to a 50-ml. three-necked flask equipped with a distillation adapter and a thin capillary as a nitrogen inlet. The mixture was stirred in a nitrogen atmosphere for 1 hour at room temperature. The pressure was then reduced to 50 millitorr and the mixture was heated to 128° C. over 1 hour, whereupon 2-ethyl-1-hexanol was removed by distillation. The residue was the desired di-(2-ethyl-1-hexyl)2,2-diethylpropane-1,3-dioxytitanate, the compound of formula VIII. The yield was 5.80 grams, or 96.1% of theoretical.

Similar methods were employed to prepare the compounds of formulas III–VII and IX–XI. All were clear liquids except IV, which was a hazy liquid, and III, V and VII, which were pastes.

EXAMPLE 2

The apparatus of Example 1 was employed for the reaction of 5.448 grams (9.647 mmol.) of tetra-2-ethyl-1-hexyl titanate with 3.092 grams (19.29 mmol.) of 2-(1-butyl)-2-ethyl-1,3-propanediol at 90° C. and a pressure of 50 millitorr. The viscous residue solidified upon cooling. It was triturated with hexane to afford the desired bis[2-(1-butyl)-2-ethyl-1,3-propylene]titanate, the compound of formula XV, as a solid having a melting point of 314°–317° C. The yield was 3.33 grams, or 94.7% of theoretical.

The method of Example 2 was also employed for the preparation of the compounds of formulas XII–XIV, all of which were solids melting above 330° C.

EXAMPLE 3

The procedure of Example 2 was employed for the reaction of 6.526 grams (19.18 mmol.) of tetra-1-butyl titanate with 5.608 grams (38.35 mmol.) of 2-ethyl-1,3-hexanediol at 90°–100° C. and 20 millitorr. The product, a white powder, was the desired bis(2-ethyl-1,3-hexylene)titanate, the compound of formula XVI. It melted at

EXAMPLE 4

The apparatus of Example 1 was employed for the reaction of 9.671 grams (17.12 mmol.) of tetra-2-ethyl-1-hexyl titanate with 2.373 grams (17.68 mmol.) of 2,2-bis(hydroxymethyl)-1-butanol, at 0.5 millitorr under distillation conditions. The desired 1-(1-butoxy)-4-methyl-2,6,7-trioxa-1-titanabicyclo[2.2.2]octane, the compound of formula XVII, was obtained as a white crystalline solid with a melting point of 360°–365° C. The yield was 4.96 grams, or 91% of theoretical.

A similar method was employed for the preparation of the compounds of formulas XVIII–XXI, all of which were solids melting above 360° C. with decomposition.

EXAMPLE 5

The apparatus of Example 1 was employed for the reaction of 32.056 grams (56.76 mmol.) of tetra-2-ethyl-1-hexyl titanate and 2.539 grams (18.92 mmol.) of 2,2-bis(hydroxymethyl)-1-butanol (hereinafter "triol"), under distillation conditions at 100 millitorr. There was obtained the desired mixed titanate (hereinafter "catalyst XXII")in liquid form; the yield was 26.36 grams (96.9% of theoretical).

Similar products were prepared from mixtures of the following molar ratios:

Catalyst XXIII—titanate/triol, 2:1;
Catalyst XXIV—titanate/triol,2.5:1;
Catalyst XXV—titanate/triol/2,2-diethyl-1,3-propanediol, 3:1:2;
Catalyst XXVI—titanate/triol/2-(1-propyl)-2-methyl-1,3-propanediol, 4:1:3;
Catalyst XXVII—titanate/triol/-2-ethyl-1,3-hexanediol, 4:1:3;
Catalyst XXVIII—titanate/triol/2,2-diethyl-1,3-propanediol, 3:1:1.

All were liquids except XXIII, which was a paste.

According to the present invention, the macrocyclic polyester oligomers are converted to high molecular weight polyesters by contact at a temperature in the range of about 160°–300° C., preferably 160°–250° C., with the titanium-containing macrocyclic polyester oligomer polymerization catalyst. The latter is typically employed in the amount of about 0.01–2.0 and preferably about 0.05–1.0 mole percent based on structural units in the oligomers. In the case of mixed catalysts such as XXIII–XXVIII, the mole percentage calculation is on the basis of a single titanium atom per molecule.

For use in such operations as liquid injection molding, the use of liquid catalysts is preferred. If a non-liquid catalyst is employed for a polymerization, it may be conveniently introduced in solution in a suitable solvent.

The polyesters of this invention have high molecular weights even when prepared from oligomer mixtures with a relatively high proportion of acidic impurities. The titanium catalysts initiate polymerization by incorporating ester units between the oxygen and carbon atoms in their molecular structure. Thus, a catalyst of formula II wherein n is 0 will afford a polyester with an $R^3$ moiety within the chain. When the catalyst is a bicyclo compound (i.e., n is 1), the polyester has a branched structure. As a rule, the titanium remains in the polyester end group but is removed upon contact with moist air.

It is within the scope of the invention to employ a mixture of catalysts of formula II, or a mixture of such a catalyst with one of another structure such as a tetraalkyl titanate, to produce a mixture of branched and linear polyesters. The proportions of the two types of catalysts may be varied to afford the desired degree of branching.

The method of this invention is illustrated by the following examples. All percentages are by weight. Molecular weights were determined by gel permeation chromatography relative to polystyrene.

EXAMPLE 6

A 25-ml. two-necked flask equipped with a vacuum adapter and a nitrogen inlet was charged with 5 grams (22.7 mmol. based on structural units) of macrocyclic poly(butylene terephthalate) oligomers. The oligomers were dried by heating at 100° C. under vacuum for ½ hour, after which the temperature was raised to 190° C. and stirred for 15 minutes to melt the oligomers. Nitrogen was passed into the flask to bring it to atmospheric pressure, after which 38.2 mg, (0.114 mmol., 0.5 mole percent) of compound XVI, in the form of an 18.6% solution in o-dichlorobenzene, was injected into the melt using a micro-syringe. The melt became very viscous and the polymer crystallized within 10 minutes. The mixture was maintained at 190° C. for an additional 20 minutes and was then cooled to room temperature. It was the desired linear polyester and had weight average and number average molecular weights of 303,600 and 129,800, respectively.

EXAMPLE 7

Following the procedure of Example 6, 50 microliters (114 mmol.) of catalyst VIII as a liquid (without solvent) was injected into a 5-gram sample of macrocyclic poly(butylene terephthalate) oligomers and polymerization was allowed to proceed. The product was a linear polyester having weight average and number average molecular weights of 111,200 and 35,200, respectively.

EXAMPLE 8

Following the procedure of Example 6, a mixed macrocyclic oligomer mixture comprising 95 mole percent poly(butylene terephthalate) and 5 mole percent poly(ethylene terephthalate) was polymerized by the addition of a 17.2% solution in o-dichlorobenzene of catalyst XX. The resulting branched polyester had weight average and number average molecular weight of 285,000 and 58,500, respectively.

EXAMPLES 9–14

Following the procedure of Example 7, macrocyclic poly(butylene terephthalate) oligomers were polymerized to mixtures of linear and branched polyesters by the addition of various catalysts in the amount of 0.5 mole percent. The results are given in the following table.

| Example | Catalyst | Mw | Mn |
| --- | --- | --- | --- |
| 9 | XXII | 109,300 | 32,300 |
| 10 | XXIV | 124,100 | 37,700 |
| 11 | XXV | 151,800 | 43,100 |
| 12 | XXVI | 133,000 | 39,500 |
| 13 | XXVII | 127,300 | 39,600 |
| 14 | XXVIII | 135,500 | 39,700 |

In a control experiment conducted under identical conditions with the use of tetra-2-ethylhexyl titanate, poly(butylene terephthalate) having weight and number average molecular weights of 62,700 and 24,700, respectively, was obtained. Thus, the polyesters of the present invention have substantially higher molecular weights than polyesters prepared using tetraalkyl titanates.

What is claimed is:

1. A method for preparing a polyester which comprises contacting, at a temperature within the range of about 160°–300° C., at least one macrocyclic polyester oligomer comprising structural units of the formula

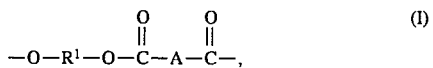

wherein $R^1$ is an alkylene or mono-or polyoxyalkylene radical containing a straight chain of about 2–8 atoms and A is a m- or p-linked monocyclic aromatic or alicyclic radical, with at least one titanium-containing macrocyclic polyester oligomer polymerization catalyst having, at least in part, the formula

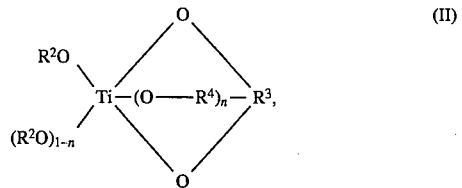

wherein:

$R^2$ is an alkyl radical, or the two $R^2$ radicals taken together form a divalent saturated aliphatic hydrocarbon radical;

$R^3$ is a $C_{2-10}$ divalent or trivalent saturated aliphatic hydrocarbon radical;

$R^4$ is a methylene or ethylene radical; and n is 0 or 1.

2. A method according to claim 1 wherein $R^2$ is $C_{1-10}$ primary or secondary alkyl.

3. A method according to claim 2 wherein n is 0.

4. A method according to claim 2 wherein n is 1.

5. A method according to claim 4 wherein $R^4$ is methylene.

6. A method according to claim 2 wherein $R^3$ is a $C_{3-10}$ radical.

7. A method according to claim 6 wherein $R^3$ has a chain of three carbon atoms separating the oxygen atoms.

8. A method according to claim 1 wherein the $R^2$ radicals together form a $C_{3-10}$ saturated aliphatic hydrocarbon radical.

9. A method according to claim 8 wherein the two $R^2$ radicals form a branched hydrocarbon radical.

10. A method according to claim 1 wherein the macrocyclic polyester oligomer is macrocyclic poly(ethylene terephthalate), macrocyclic poly(butylene terephthalate) or a copolymer thereof.

11. A method according to claim 1 wherein the proportion of catalyst is about 0.01–2.0 mole percent based on structural units in the oligomers.

12. A method according to claim 1 wherein the catalyst contains tetraalkyl titanate species and bicyclo species of formula II in which n is 1, and is prepared by the reaction of 2–3 moles of a tetraalkyl titanate with 1 mole of a triol of the formula

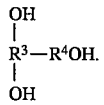

* * * * *